United States Patent
Moctezuma de La Barrera

(10) Patent No.: US 7,392,076 B2
(45) Date of Patent: Jun. 24, 2008

(54) SYSTEM AND METHOD OF REGISTERING IMAGE DATA TO INTRA-OPERATIVELY DIGITIZED LANDMARKS

(75) Inventor: José Luis Moctezuma de La Barrera, Freiburg (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 668 days.

(21) Appl. No.: 10/701,335

(22) Filed: Nov. 4, 2003

(65) Prior Publication Data

US 2005/0096535 A1 May 5, 2005

(51) Int. Cl.
*A61B 5/05* (2006.01)

(52) U.S. Cl. .................... 600/427; 600/407; 600/424

(58) Field of Classification Search .......... 606/88, 606/130; 600/424, 427, 428, 407; 382/128
See application file for complete search history.

(56) References Cited

U.S. PATENT DOCUMENTS

| | | | | |
|---|---|---|---|---|
| 4,841,975 A * | 6/1989 | Woolson | ...................... | 600/425 |
| 5,007,936 A | 4/1991 | Woolson | ...................... | 623/23 |
| 5,383,454 A * | 1/1995 | Bucholz | ...................... | 600/429 |
| 5,520,694 A * | 5/1996 | Dance et al. | ................... | 606/88 |
| 5,611,353 A | 3/1997 | Dance et al. | ................. | 128/782 |
| 5,617,857 A * | 4/1997 | Chader et al. | ................ | 600/424 |
| 5,682,886 A * | 11/1997 | Delp et al. | ................... | 600/407 |
| 5,880,976 A | 3/1999 | DiGioia, III et al. | ........ | 364/578 |
| 6,002,859 A * | 12/1999 | DiGioia et al. | ................ | 703/11 |
| 6,100,856 A * | 8/2000 | R.ang.be | ...................... | 343/882 |
| 6,161,080 A * | 12/2000 | Aouni-Ateshian et al. | .... | 703/11 |
| 6,205,411 B1 | 3/2001 | DiGioia, III et al. | .......... | 703/11 |
| 6,514,259 B2 | 2/2003 | Picard et al. | ................... | 606/88 |
| 6,595,997 B2 | 7/2003 | Axelson, Jr. et al. | .......... | 606/88 |
| 6,607,487 B2 | 8/2003 | Chang et al. | ................. | 600/437 |
| 6,697,664 B2 * | 2/2004 | Kienzle III et al. | .......... | 600/427 |
| 6,711,432 B1 * | 3/2004 | Weiss et al. | .................. | 600/427 |
| 6,928,742 B2 * | 8/2005 | Broers et al. | ................... | 33/512 |
| 2002/0107522 A1 | 8/2002 | Picard et al. | ................... | 606/88 |
| 2002/0116067 A1 | 8/2002 | Mears et al. | ................ | 623/22.4 |
| 2002/0193797 A1 | 12/2002 | Johnson et al. | ................ | 606/79 |
| 2002/0198451 A1 * | 12/2002 | Carson | ........................ | 600/424 |
| 2003/0153829 A1 | 8/2003 | Sarin et al. | .................... | 600/426 |
| 2004/0034302 A1 * | 2/2004 | Abovitz et al. | .............. | 600/428 |
| 2004/0106916 A1 * | 6/2004 | Quaid et al. | .................... | 606/1 |
| 2004/0152970 A1 * | 8/2004 | Hunter et al. | ................ | 600/424 |

OTHER PUBLICATIONS

*Total Knee Replacement—Computer-Assisted Surgical System Uses A Calibrated Robot*, IEEE Engineering in Medicine and Biology, May/Jun. 1995 (pp. 301-306).
*A Computer-Assisted Total Knee Replacement Surgical System Using a Calibrated Robot* at http://lims.mech.northwestern.edu/~peshkin/pubs/1995 ComputerAssistedTKR.pdf., (pp. 1-28).

* cited by examiner

*Primary Examiner*—Brian L. Casier
*Assistant Examiner*—Iman Kenneth Kholdebairn
(74) *Attorney, Agent, or Firm*—McCracken & Frank LLP

(57) ABSTRACT

A two dimensional image is registered with mechanical axis data, and possibly other data, using a surgical navigation system. This provides the user with additional graphical information on a display screen as the procedure is performed. The mechanical axis data can be generated using an anatomical assessment.

18 Claims, 14 Drawing Sheets

SYSTEM AND METHOD OF REGISTERING IMAGE DATA TO INTRA-OPERATIVELY DIGITIZED LANDMARKS

FIELD OF THE INVENTION

The present invention relates to a system and a method for registering two dimensional image data to intra-operatively digitized landmarks. More particularly, this invention relates to a system and method for registering two dimensional image data to intra-operatively digitized landmarks in the context of joint replacement surgery and particularly knee replacement surgery using a surgical navigation system.

BACKGROUND OF THE INVENTION

Joint replacement surgery, also known as total joint arthroplasty, is performed on individuals who have a joint that because of arthritis or other condition or injury requires a replacement or reshaping of the joint surfaces. Typical knee replacement surgery involves the shaping of the distal femoral bone using a special cutting jig that has been placed on the end of the femur. The cutting jig is aligned with the mechanical axis of the leg so that the replacement knee is properly aligned, even if the patient was originally knock-kneed or bowlegged. The distal end of the femur is cut and shaped to accept an implant surface to function as part of the replacement knee. In addition, the tibia is prepared in a similar manner using another special cutting jug to assist the surgeon in making a resection of the tibia so that the implant will be properly aligned in the new knee. Also, the patella is prepared by typically removing a portion of the undersurface of the patella. In a similar manner, hip replacement surgery involves the preparation of the acetabular cup to receive a replacement surface and the femoral head is replaced with a stem and ball to match the cup implanted into the acetabulum. For the shoulder, the glenoid is not usually replaced but the surface is modified to accept an implant placed in the end of the humerus bone.

After the bones surfaces and/or the tissue has been prepared, the implants are then placed into position on the prepared surfaces. For instance, in knee replacement surgery, in addition to implants on the surfaces of the prepared femur and tibia, the replacement knee joint also typically will include a spacer to mimic the effect of the knee cartilage. Often a surgeon will first insert temporary or trial implants into position within the prepared joint and then manipulate the joint to be sure the implants will function properly and the joint will be stable and have a sufficient range of motion.

Orthopedic surgeons have been using surgical navigation systems for some time to assist in properly locating and positioning the cutting jigs used to make the resections of the bone to prepare the joints to accept the replacement implants. However, in the past the use of a surgical navigation system required the surgeon to insert markers that could be seen by the pre-operative scans and were visible to the surgeon so that the surgeon could register the pre-operative scan to the patient's leg and knee joint during surgery. This has involved either semi-permanent markers or fiducials placed into the patient's tissue before the preoperative scans are made and requiring that the patient maintain the fiducials in place until surgery, or temporary fiducials that are removed after the pre-operative scan is done and replace just prior to surgery. Each of these systems has disadvantages. While the use of the semi-permanent fiducials insures proper registration of the scan to the patient's leg and joint, there can be significant discomfort in the insertion and maintenance of the fiducials in place between the time of the scan and the date of surgery. The use of the temporary fiducials eliminates this problem, but these temporary fiducials are not as reliable since they must be replaced in exactly the same positions for proper registration to occur. In each of these surgeries and in other related surgeries, it is now possible to perform these surgeries using digitized landmarks that are determined intra-operatively without the need to have a pre-operative scan. However, it is desirable to incorporate images into the display screens used by the surgeons to locate the jigs and other cutting tools so that the proper resections of the bone are made to receive the implants to repair the joint. In this instance, the image is used as a background guide and the image is not used as the basis for accurately positioning the tools and jigs.

SUMMARY OF THE INVENTION

One aspect of the present invention relates to a system for registering two dimensional image data to intra-operatively digitized landmarks obtained during a joint arthroplasty procedure on a patient having a joint in need of such a procedure that includes a surgical navigation system capable of determining a position and an orientation of an object within a working volume, including a central processing unit, a display, a memory unit and a storage unit. The system also has means for importing the two dimensional image data for the joint into the memory unit; and means for performing an intra-operative anatomical survey of the joint and a limb associated with the joint to digitize selected landmarks and determining the mechanical axis of the limb. Further, the system includes means for registering the two dimensional image data to the mechanical axis and displaying a the registered image of the mechanical axis and the two dimensional image data on the display; and means for assisting in guiding a cutting jig into position within the joint based on the landmarks while showing the registered two dimensional image data in relation to the landmarks, wherein the position and the orientation of the cutting jig can be tracked by the surgical navigation system.

A further aspect of the present invention relates to a method for registering two dimensional image data to intra-operatively digitized landmarks obtained during a joint arthroplasty procedure on a patient having a joint in need of such a procedure, the method comprising the steps of: importing the two dimensional image data for the joint into memory of a surgical navigation system capable of determining the position and orientation of an object within a working volume wherein the surgical navigation system includes a display, a central processing unit and storage; performing an anatomical survey of the joint and an associated limb; digitizing selected landmarks based on the anatomical survey; determining a mechanical axis for the limb based on the digitized landmarks, registering the image data to the mechanical axis, and displaying the registered two dimensional image data and mechanical axis on the display; and guiding a cutting jig into position within the joint using the surgical navigation system based on the landmarks.

DETAILED DESCRIPTION OF THE DRAWINGS

Figure 1:
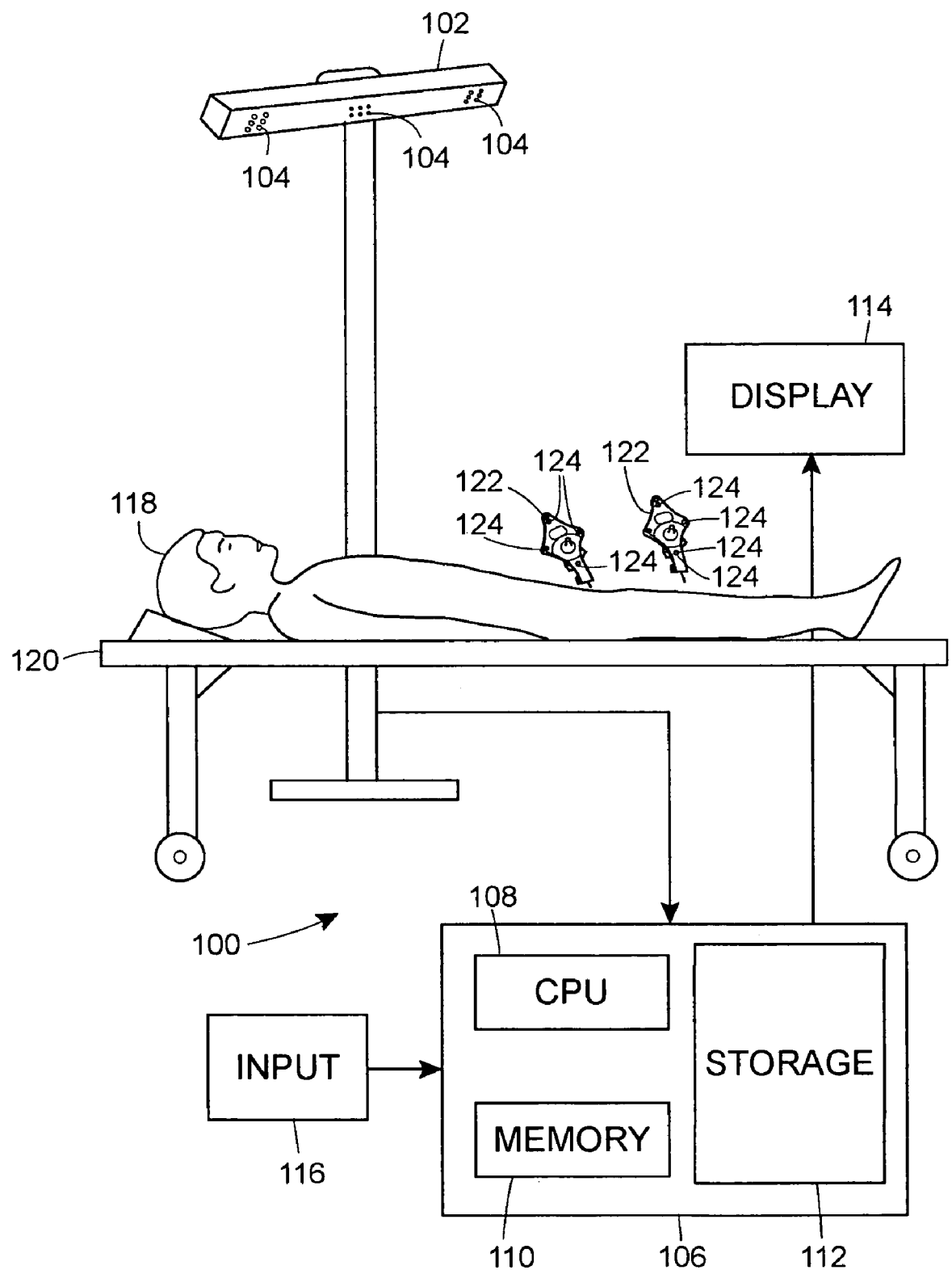
FIG. 1 is a schematic view of a surgical navigation system useful in the method of the present invention.

Referring to FIG. 1, a surgical navigation system 100 includes a camera 102 having a series of light sensitive arrays 104. Each of the light sensitive arrays 104 is capable of detecting light within a predetermined wavelength such as infra red light. The surgical navigation system 100 also includes a computer 106 having an internal central processing unit (CPU) 108, an internal memory unit 110 and an internal storage unit 112. The computer 106 can be any of a number of conventional commercially available computers running a variety of commercially available operating systems such as Windows, Unix, Mac OS, and the like. The computer 106 also includes a display device 114, such as any of the conventional commercially available monitors. The computer 106 also includes any or all of a series of input devices 116 such as keyboards, pointing devices, and the like. As discussed hereinafter, certain smart instruments that can be tracked by the surgical navigation system 100 are also capable of acting as the input devices 116.

Figure 5:
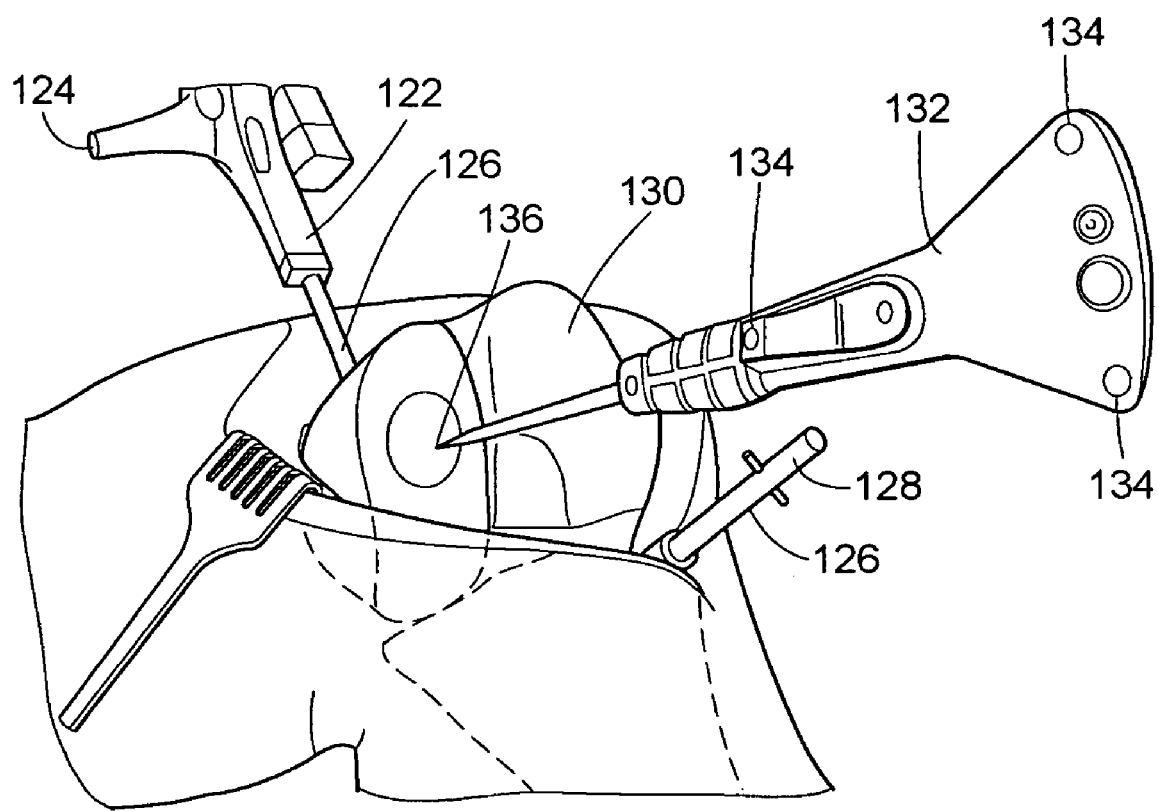
FIG. 5 is a view of a knee partially opened for surgery showing the direct digitization of points within the knee.

A patient 118 is placed on an operating room table 120 and prepared for the surgical procedure. Part of the preparation for the surgical procedure can include attaching a series of tracking devices 122 that are visible to the light sensitive arrays 104 in the camera 102. The tracking devices 122 have a series of light emitting diodes (LED's) 124 that transmit infra red light. The LED's 124 will individually flash in response to commands from the surgical navigation system 100 in a known manner. In this way the surgical navigation system 100 can determine the position and orientation of each of the tracking devices 124 and by known methods determine the position and orientation of the bone to which the individual tracking device 124 has been attached. For a total knee arthroplasty typically multiple tracking devices 124 will be attached to the patient. As shown in FIG. 5, the tracking devices 124 are attached to the patient 118 by a post 126 that has a quick release connection 128 that mates with a corresponding known quick release structure (not shown) in the tracking device 124. Examples of tracking devices and surgical navigation systems suitable for use in the present invention are shown in U.S. Published Application 2001/0034530, published Oct. 25, 2001, the disclosure of which is incorporated by reference.

Figure 2:
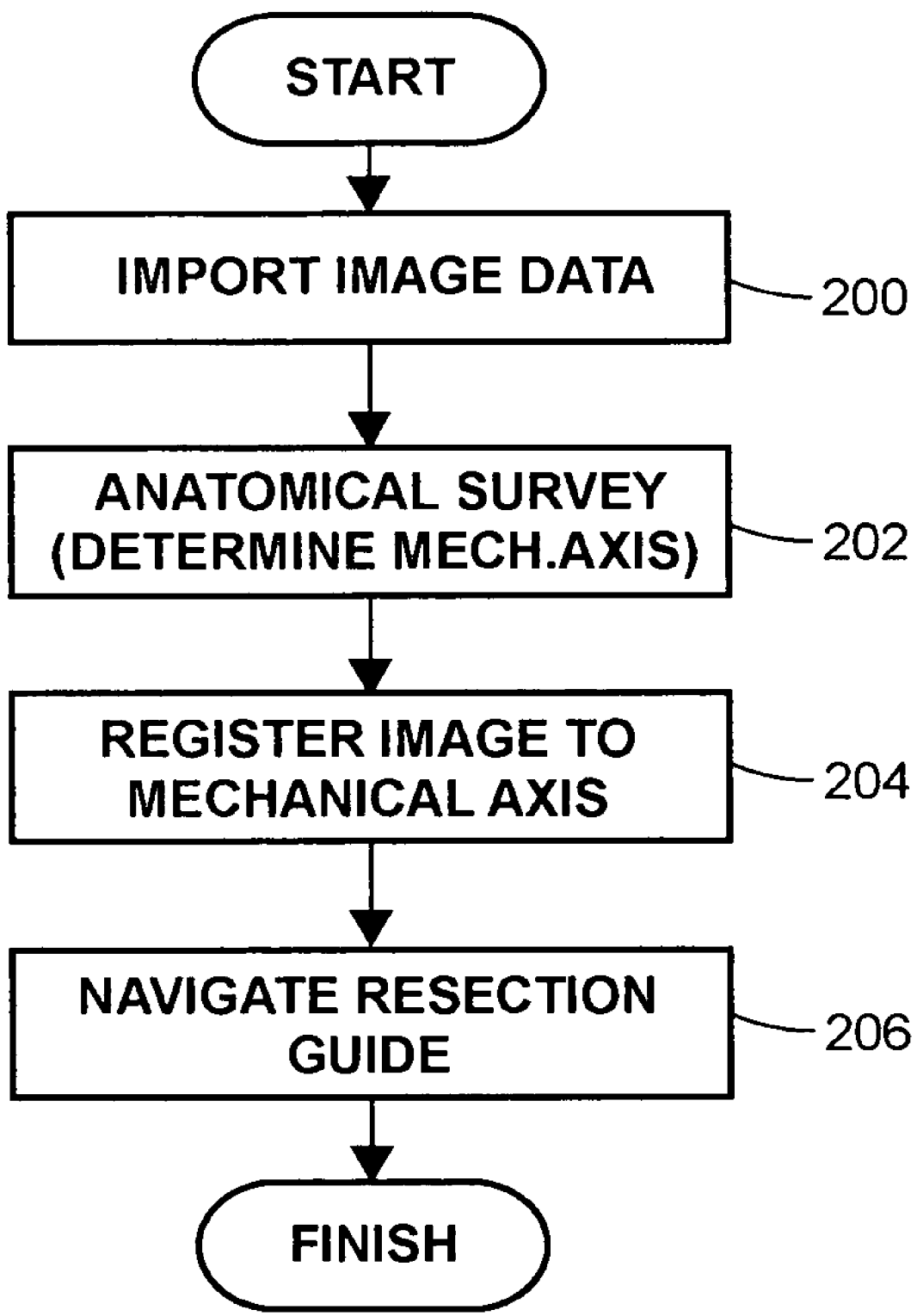
FIG. 2 is a flow diagram of a system to accomplish one embodiment of the method and system of the present invention.
Figure 3:
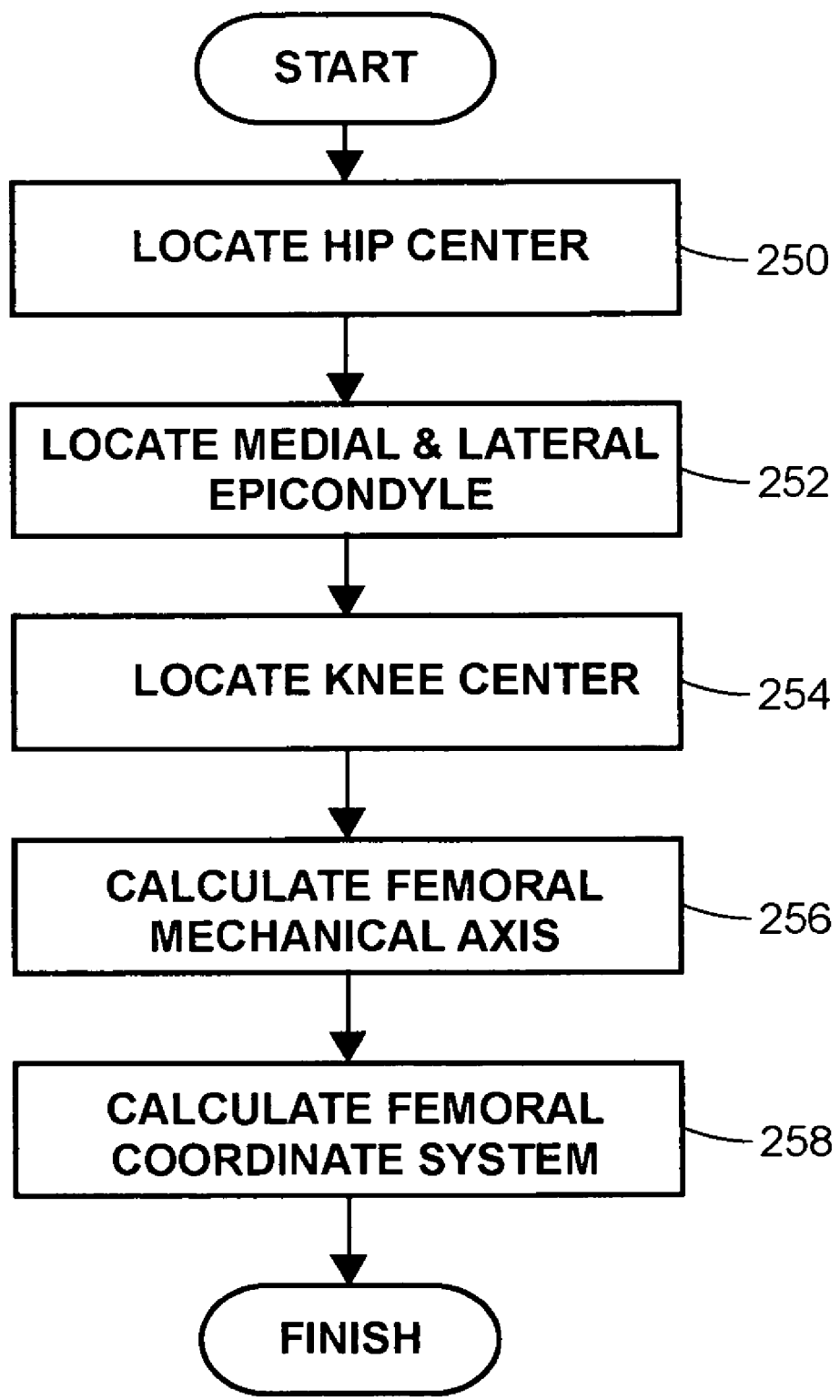
FIG. 3 is a flow diagram of an anatomical survey of the femur useful in the system and method of the present invention.
Figure 9:
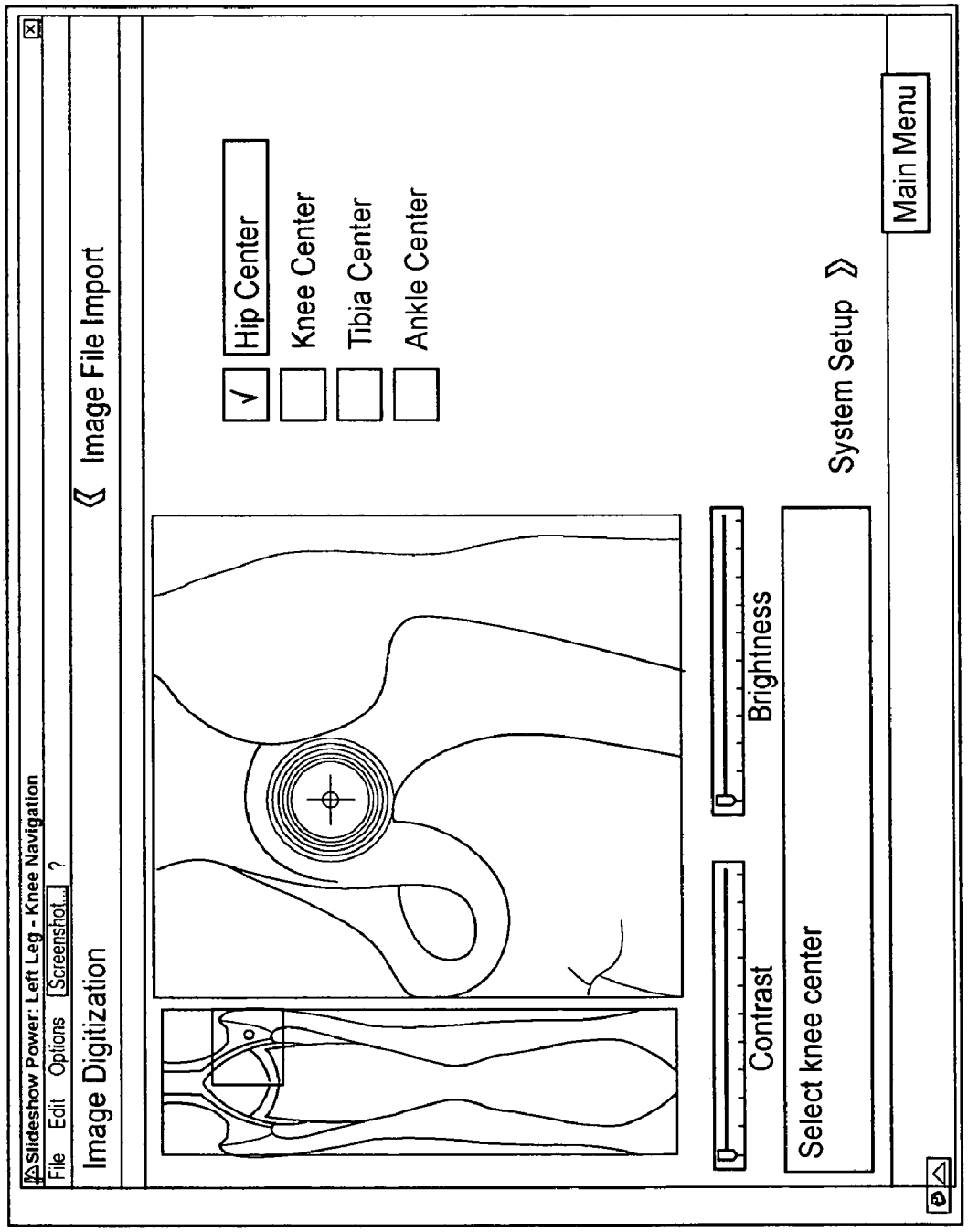
FIG. 9 is a diagrammatic view of a display screen showing further aspects of the method and system of the present invention.

FIG. 2 shows an overview flow diagram of one embodiment of the method and the system of the present invention. The process begins and control passes to a block 200 that imports an image into the memory unit 110. The image can be a simple two dimensional x-ray scan of the joint and attached limb that is the subject of the surgical procedure. Typical x-ray scans, such as AP (anterior posterior) scans, are taken prior to surgery. The scan is also one that can be taken in the operating room for the purpose of adding visualization to the procedure. The control then passes to a block 202 that guides the surgeon in performing an anatomical assessment of the subject joint. One of the outcomes from the anatomical assessment performed by the block 202 is the location of the mechanical axis of the limb in question. It should be noted at this point that the order of the process blocks 200 and 202 is not important and the process of the block 202 can be performed either after or before the process step of the block 200. At this point, control will pass to a block 204 that registers the image imported by the block 200 with the mechanical axis determined by the block 202. The registration performed by the block 204 first identifies the appropriate mechanical axis of the limb or limbs if the joint is connected to two limbs and the respective coordinate systems. The surgical navigation system 100 then matches the mechanical axis with the best fit for the mechanical axis on the structure shown in the two dimensional image. As part of this best fit, the surgical navigation system 100 identifies the various landmarks on the image and matches these landmarks and the coordinate system created during the anatomical survey. If necessary, the surgical navigation system 100 will enlarge or shrink the image to match the dimensions of the mechanical axis and the distance between appropriate landmarks. The surgical navigation system will then in a block 206 provide visual assistance to the surgeon to position a resection guide into a desired position. The surgical navigation system 100 will utilize the registered image created by the block 204 to provide a visual background to the AP images displayed on the display 114. The surgical navigation system 100 is capable to providing complete navigation and position assistance to the surgeon to locate the resection guide based on the data determined by the anatomical assessment alone. The registration of the image to the mechanical axis provides the surgical navigation systems with the ability to utilize standard low-resolution images to provide additional information and background FIG. 3 shows a block diagram of an anatomical survey of a femur to determine the mechanical axis of the femur. The process begins at a block 250 that locates the hip center. The hip center can be located by known methods such as manipulating the femur having the tracking device 122 attached to the distal end of the femur and recording the locations of the tracking device 122 and using these recorded locations determine the center point of the sphere. The center point of the sphere is the center of the hip joint. This method is disclosed in U.S. Pat. No. 5,611,353, the disclosure of which is incorporated by reference. The control then passes to a block 252 that locates the medial and lateral epicondyle of the femur. These points are typically located after the knee joint has been opened for surgery as shown in FIG. 5 and a femoral surface 130 is digitized using a pointer 132 having similar LED's 134 to the LED's 124 on the tracking devices 122. The pointer 132 has a tip 136 that is placed in contact with specific points on the femoral surface 130. When the tip 136 is in position the pointer 132 is activated in a known manner and the position information or the tip 136 is transmitted to the surgical navigation system 100. The locations of the medial and lateral epicondyles can be done either by direct digitization or by a morphologic analysis. The direct digitization method relies of the surgeon being able to identify the structure on the femur of the patient 118 that corresponds to the medial epicondyle and the lateral epicondyle. The surgeon touches the tip 136 of the pointer 132 to the appropriate structure and activates the pointer to record the location. The surgical navigation system will indicate the location on the display 116 and if the surgeon is satisfied with the result, the surgeon can proceed to digitize the lateral epicondyle. The location of the lateral epicondyle is digitized in the same manner as the medial epicondyle. The morphologic analysis has the surgeon digitize the femoral surface 130 and the system will determine the location of the medial and lateral epicondyles from the digitization of the femoral surface 130. Once the locations of the medial and lateral epicondyles are identified, the location of the transepicondylar axis is determined. The transepicondylar axis is a line between the medial epicondyle and the lateral epicondyle. The process next proceeds to a block 254 that determines the location of the center of the knee. This determination is done by either a single point digitization of the knee center or by a morphologic analysis to generate a calculated knee center. Using the direct digitization method, the surgeon uses the pointer 132 and touches the tip 136 to the structure in the knee corresponding to the knee center and activates the pointer in the same manner as the digitization of the epicondyles above. The morphologic analysis of the knee center is performed in a manner similar to the analysis of the epicondyles discussed above. The surgeon can choose either method to digitized the locations of the epicondyles and the knee center during the setup of the surgical navigation system 100. Once the location of the knee center has been determined, the process goes next to a block 256 that determines the location of the fermoral mechanical axis. The femoral mechanical axis is the axis between the center of the hip as determined by the block 250 and the knee center as determined by the block 254. The system also will determine the femoral AP axis, the front to back or anterior to posterior axis through the femur. This can be determined by direct vector digitization using the pointer 132 or by morphologic analysis. Direct vector digitization is accomplished by visually aligning the axis of the pointer 132 with the axis or vector to be digitized. The pointer 132 is then activated, the LEDs on the pointer 132 flash, so the surgical navigation system 100 will detect the pointer orientation and register the orientation of the pointer 132 as the axis or vector. FIG. 9 is a screen shot showing in the left panel the AP image of the patient 118. Note the selection window surrounding the left hip joint. The center panel shows a magnified view of the image within the selection window on the image in the left panel. A centering icon is shown that indicates the location of the hip center based on the determination of the block 254.

At this point in the process, the system then proceeds to a block 258 that determines a femoral coordinate system. The block 258 determines the x axis of the femoral coordinate system as the femoral AP axis, the y axis as the transepicondylar axis, the z axis as the axis perpendicular to the x and y axes with the origin at the knee center. If the procedure being performed on the patient 118 is a knee replacement, the system will proceed to the anatomical survey of the tibia as described below. If the procedure is a hip replacement, no additional anatomical survey is needed. In addition, for other joints a similar anatomical survey can be performed for these joint and limb combinations.

Figure 4:
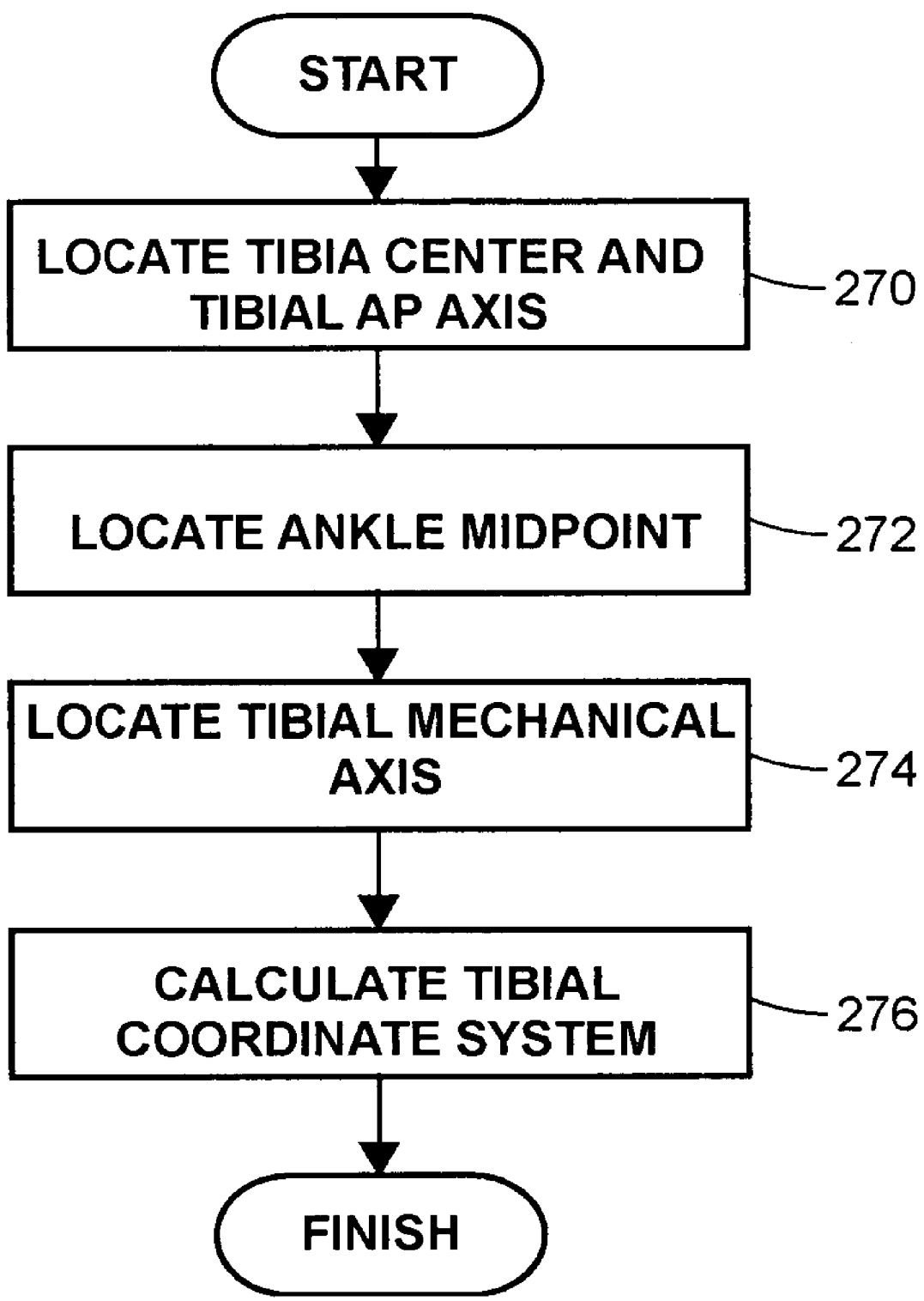
FIG. 4 is a flow diagram of an anatomical survey of the tibia useful in the system and method of the present invention.

FIG. 4 is a block diagram of a process to conduct an anatomical survey of the tibia. The process begins with a block 270 that locates a tibia center and a tibial AP axis. The tibia center is located by direct digitization using the pointer 130 and the tibial AP axis is determined by vector digitization using the pointer 130. After the tibia center and the tibial AP axis have been determined, the process next moves to a block 272 that locates the ankle midpoint. One method for locating the ankle midpoint is to perform a single point digitization of the medial malleolus and the lateral malleolus using the pointer 130. The surgeon touches the tip 134 first to the medial malleolus and activates the system to digitize the point in a known manner and then does the same to the lateral malleolus. The ankle midpoint is then determined by vector digitization of the ankle midpoint. Next the system will calculate a plane that goes through the tibia center, the medial malleolus, and the lateral malleolus. The intersection point between this plane and the ankle midpoint vector is then calculated and a preliminary tibial mechanical axis is determined. The ankle center is the intersection point of the preliminary tibial mechanical axis and the line joining the medial malleolus and the lateral malleolus. The system then passes control to a block 274 that locates the tibial mechanical axis as the axis between the determined ankle center and the tibia center. Next control passes to a block 276 that determines the tibial coordinate system. This system has the tibia center at the origin and the y axis is the tibia AP axis, the z axis is the tibial mechanical axis and the x axis is perpendicular to both the y and z axes.

Figure 10:
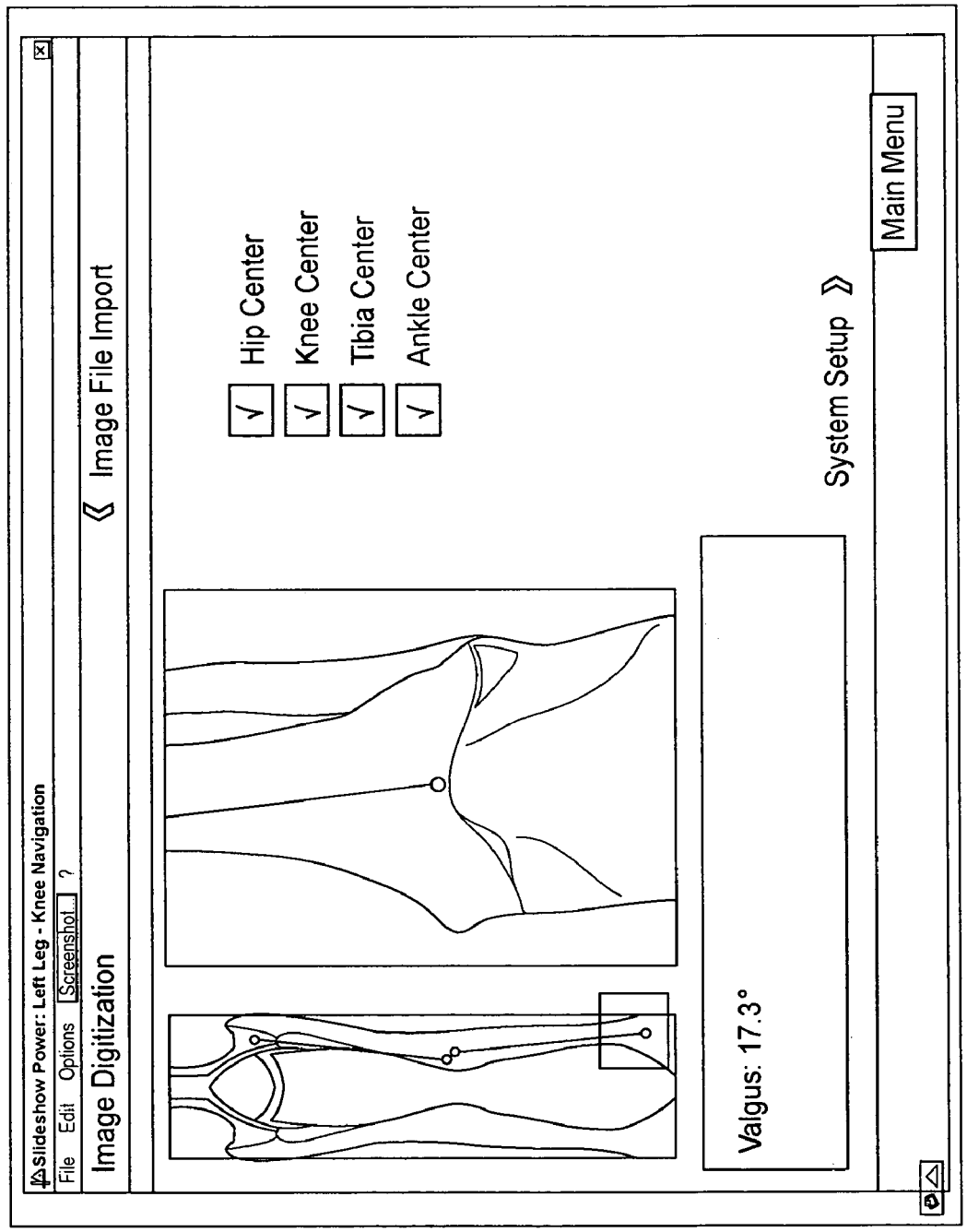
FIG. 10 is a diagrammatic view of a display screen showing additional aspects of the method and system of the present invention.

The system described in FIGS. 3 and 4 also includes checks to make sure the values determined make sense and are with a range of plausible or possible values. If a value is determined that is slightly outside the acceptable range, the user is warned the value is within a warning range and the user is given the option of redetermine the value. If the value exceeds an acceptable variance from possible, an error is displayed, the value is deleted, and the user must redetermine the value. FIG. 10 is a screen shot similar to FIG. 9 but showing the left ankle. Note that in the AP image in the left panel, the hip center and knee center locations are shown as well as the femoral mechanical axis. Also, the tibia center and the ankle center locations are also shown plus the tibial mechanical axis. The center panel also shows a magnified view of the ankle and the ankle center. The panel below the images indicates the degree of varus and valgus, in this case the valgus is 17.3°.

Figure 6:
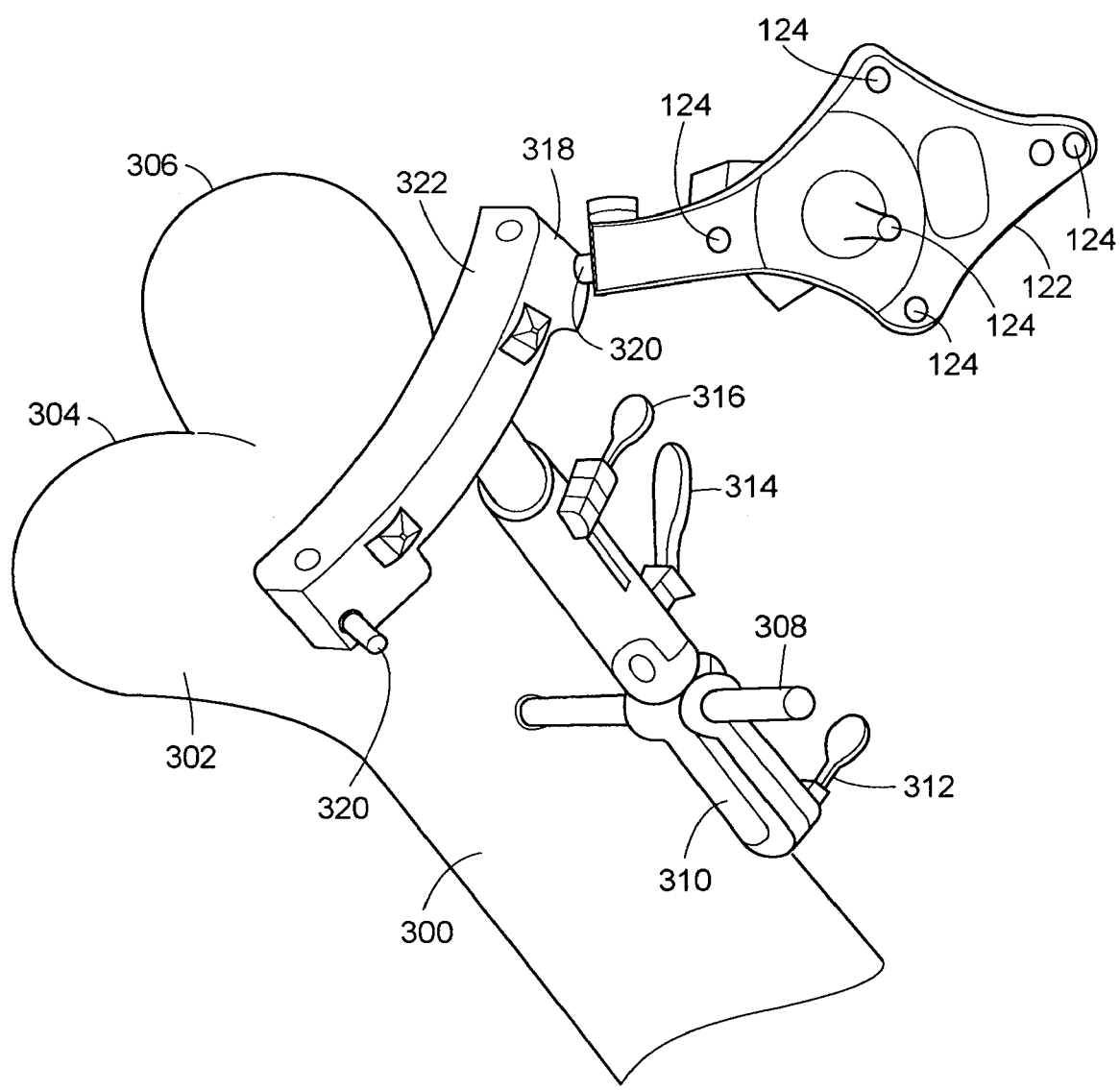
FIG. 6 is a view of a femur showing a resection guide with a tracking device attached.
Figure 11:
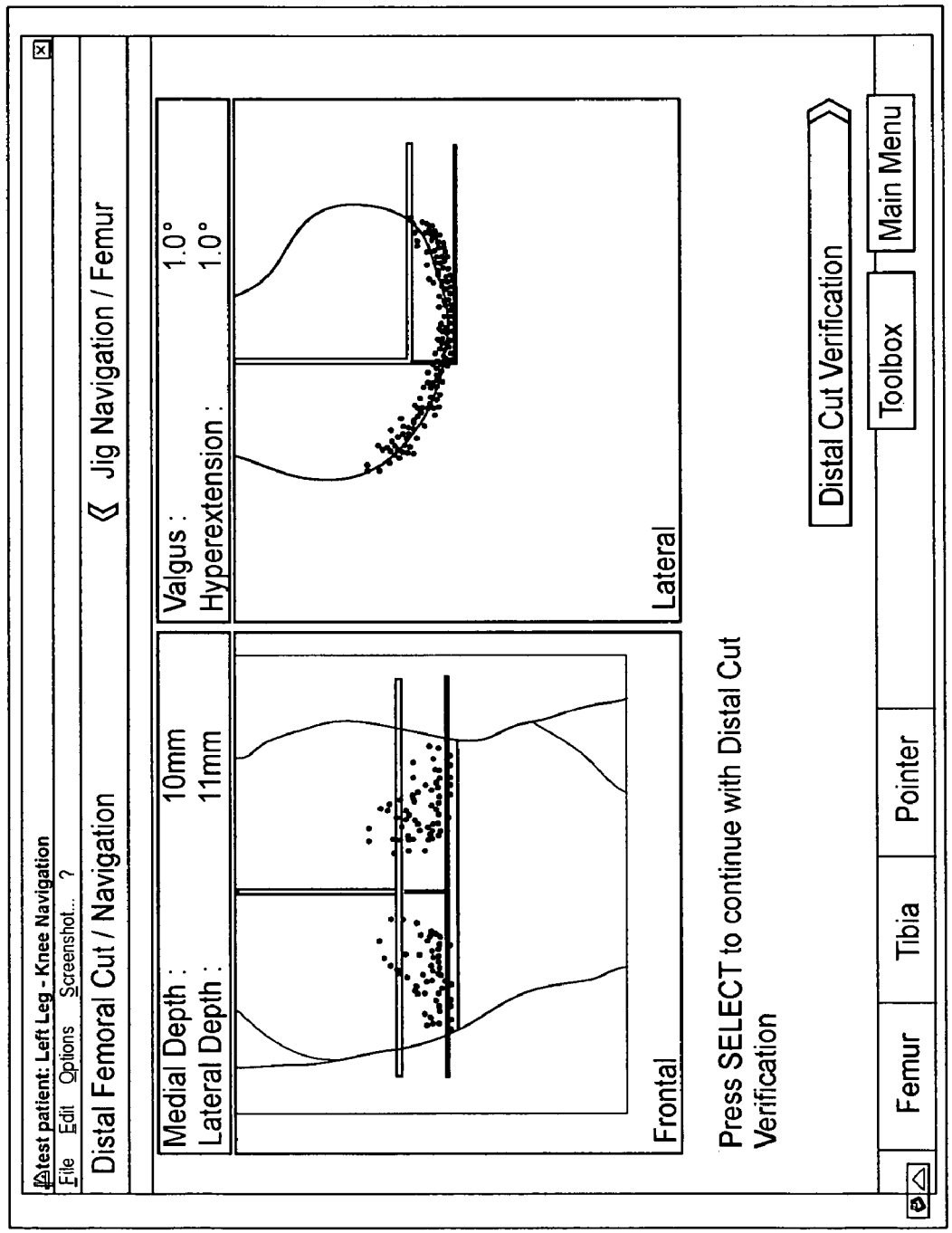
FIG. 11 is a diagrammatic view of a display screen showing still further aspects of the method and system of the present invention.
Figure 12:
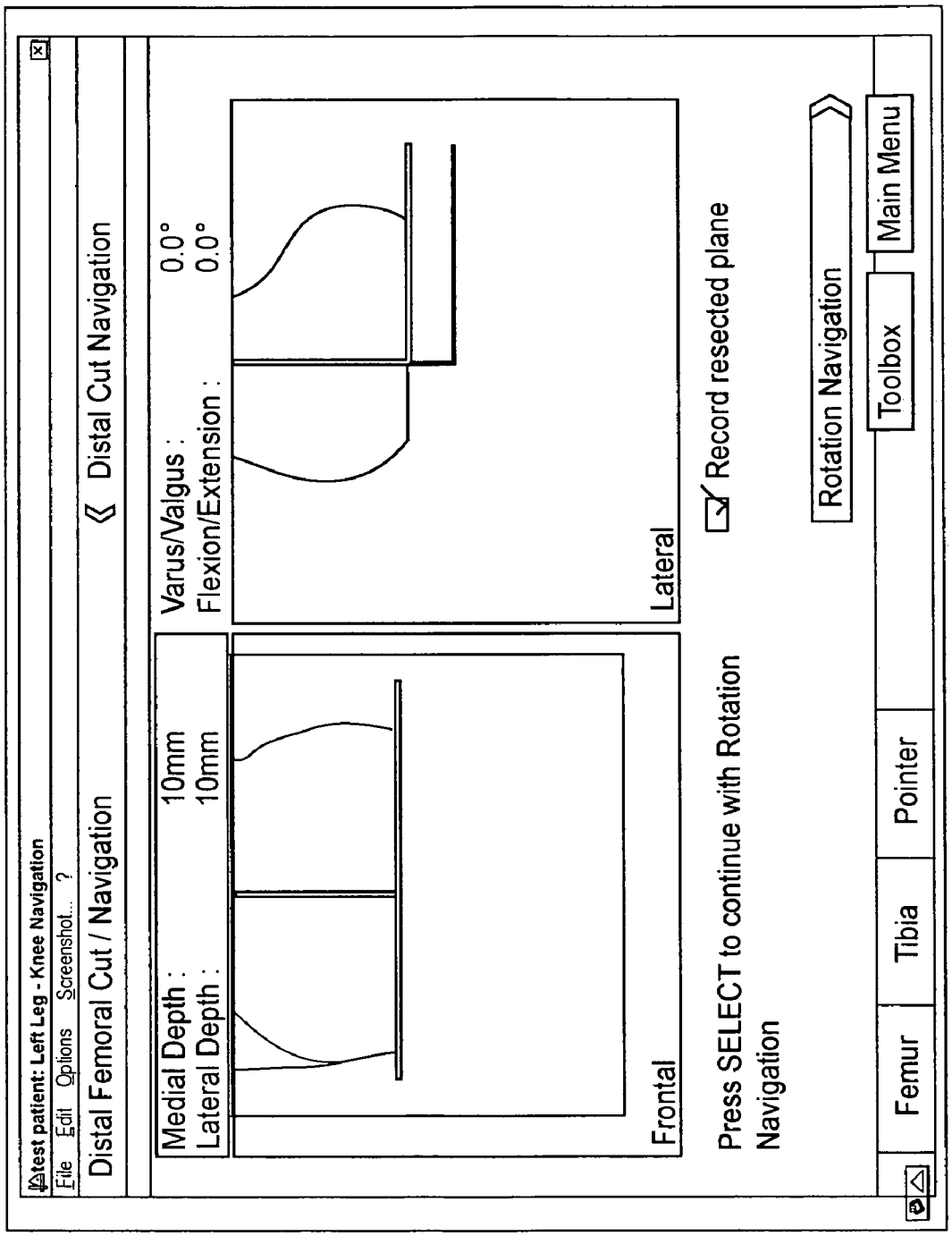
FIG. 12 is a diagrammatic view of a display screen showing other aspects of the method and system of the present invention
Figure 13:
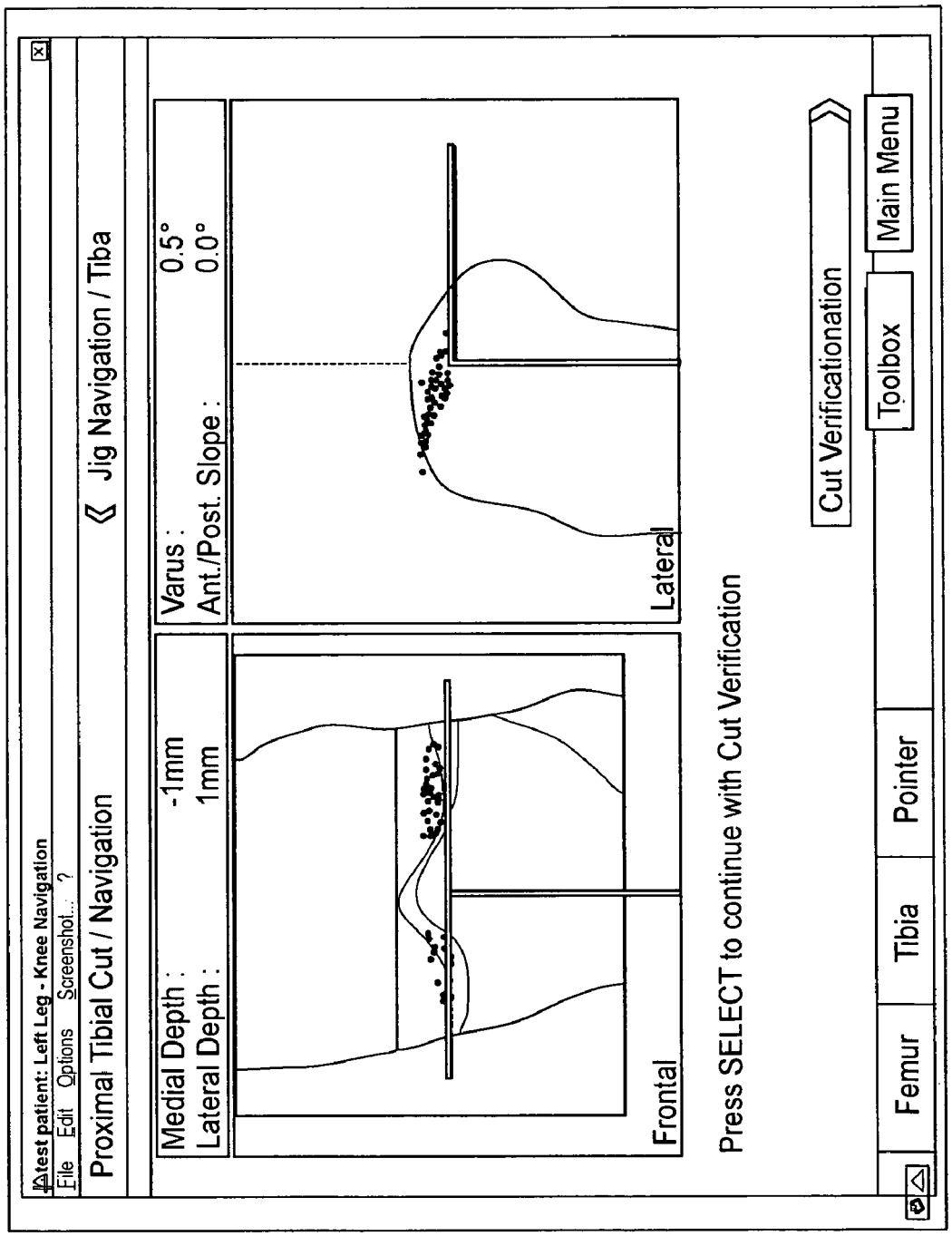
FIG. 13 is a diagrammatic view of a display screen showing still other aspects of the method and system of the present invention.
Figure 14:
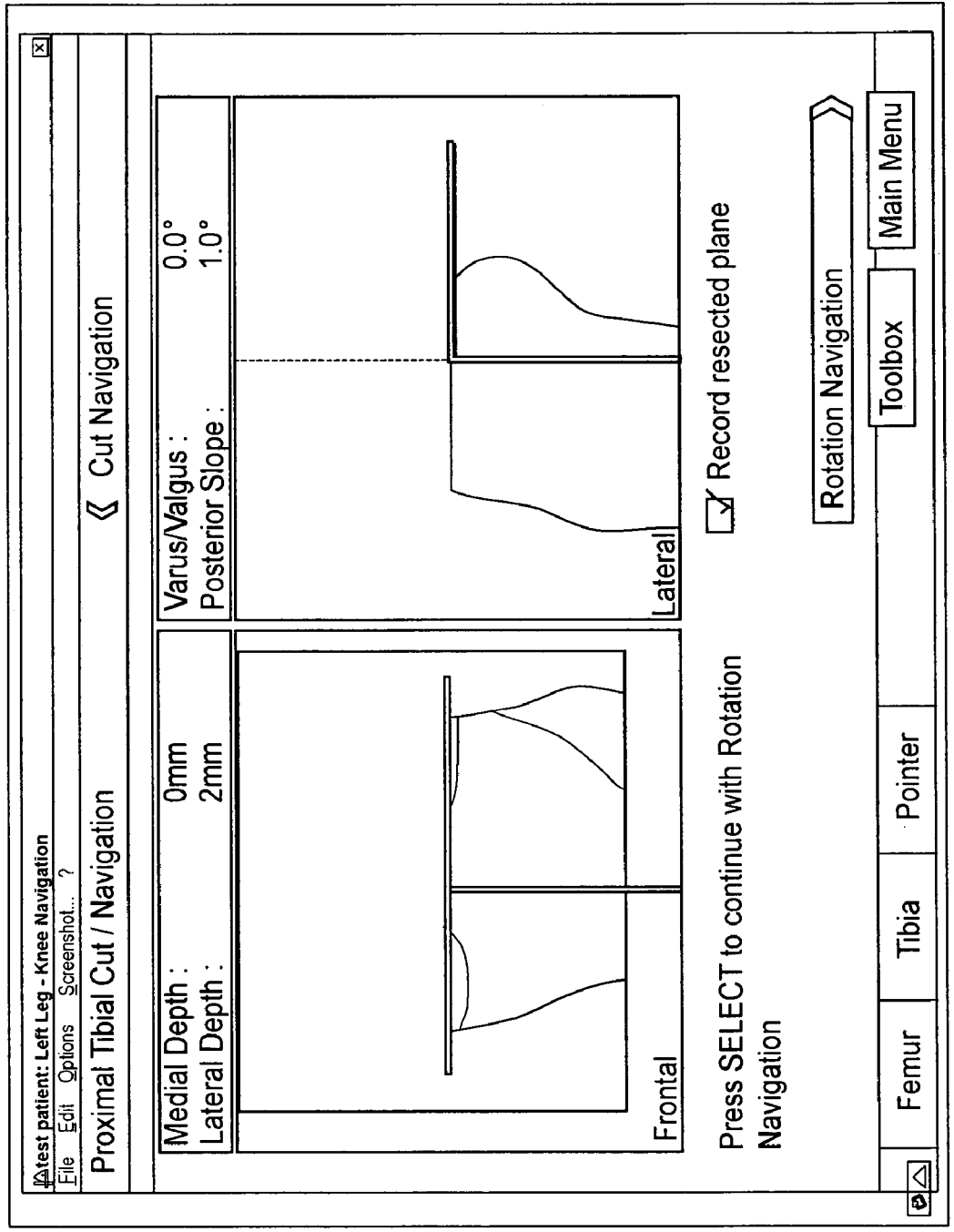
FIG. 14 is a diagrammatic view of an alternative embodiment of the present invention.

FIG. 6 shows a femur 300 having a distal end 302 with a medial epicondyle 304 and a lateral epicondyle 306. The skin tissue and the balance of the knee structure are not shown for clarity. A pin 308 is screwed into the femur 300 using a conventional surgical technique. Because the exact placement of the pin 308 is important, typically the pin 308 will be screwed into position using a surgical drill (not shown) that can be guided into position by the surgical navigation system 100. The pin 308 is place into the femur 300 on the plane of the femoral mechanical axis. An alignment guide 310 is placed over the pin 308 and the alignment guide 310 is clamped into position using clamps 312 and 314. The clamp 312 enables the alignment guide 310 to be adjusted for varus/valgus angle. The clamp 314 allows adjustment of the alignment guide 310 relative to the flexion/extension angle relative to the pin 308. The alignment guide 310 also includes a third clamp 316 that holds a resection guide 318 in place. Loosening the clamp 316 allows the resection guide 318 to be moved relative to the pin 308. The resection guide 318 also includes quick release posts 320 that mate with the quick release socket within the tracking device 122. The resection guide 318 also has a guide surface 322 to assist the surgeon in making an accurate resection of the femur 300. By attaching a tracking device 122 to the resection guide 318, the surgical navigation system 100 can assist the surgeon in the proper positioning of the resection guide 318 relative to the femur 300. FIG. 11 shows a screen shot of the navigation of the resection guide 318 to make the distal femoral cut or resection. The left panel shows the frontal view of the knee with the portion of the image shown behind the lines that indicate the femoral mechanical axis, the transepicondylar axis, and the location of the proposed resection of the femur. In the frontal view the image of the tibia is shown but is grayed out and less visible. The right frame shows the lateral view of the femur. Because the image that has been imported is a frontal AP imager, the lateral view shows a line view of the femur and the femoral AP axis and the lateral view of the proposed resection. The screen also displays other information relative to the joint including the medial and lateral depth, the varus/valgus and extension values. FIG. 12 is a verification screen similar to FIG. 11 showing the final resection plane. There is a check box showing that the resection plane will be recorded in a log file for this patient. FIGS. 13 and 14 are screen views similar to FIGS. 11 and 12, but show the tibia and the tibial resection.

Figure 7:
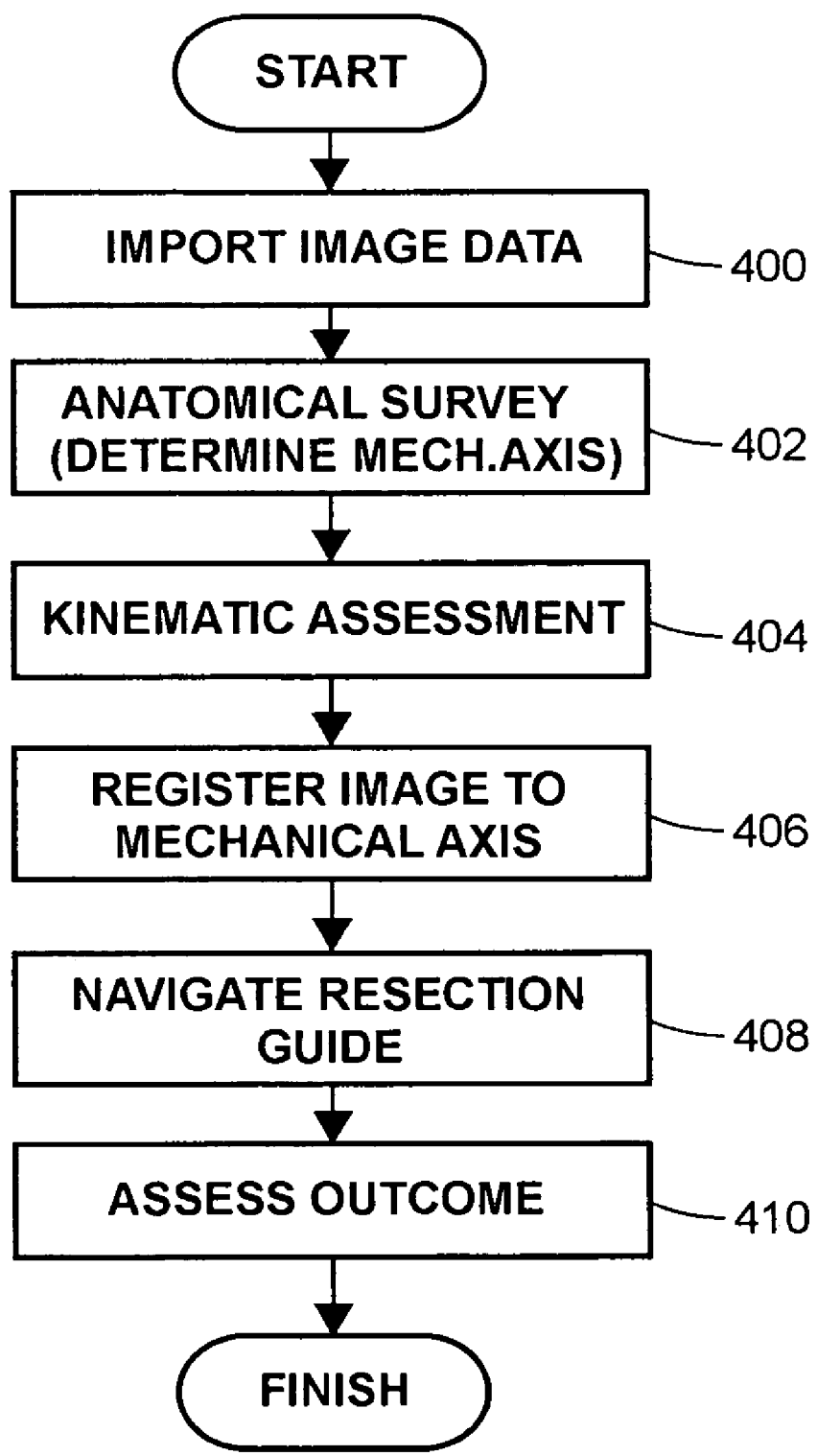
FIG. 7 is a flow diagram of a display screen showing aspects of the method and system of the present invention.

FIG. 7 is a flow diagram of an alternative process for assisting in the arthroplasty of a joint. The process begins with a block 400 that performs the same function as the block. 200 in FIG. 2. A block 402 performs an anatomical survey in a manner similar to the block 202. The process also includes a block 404 that performs a kinematic assessment.

Figure 8:
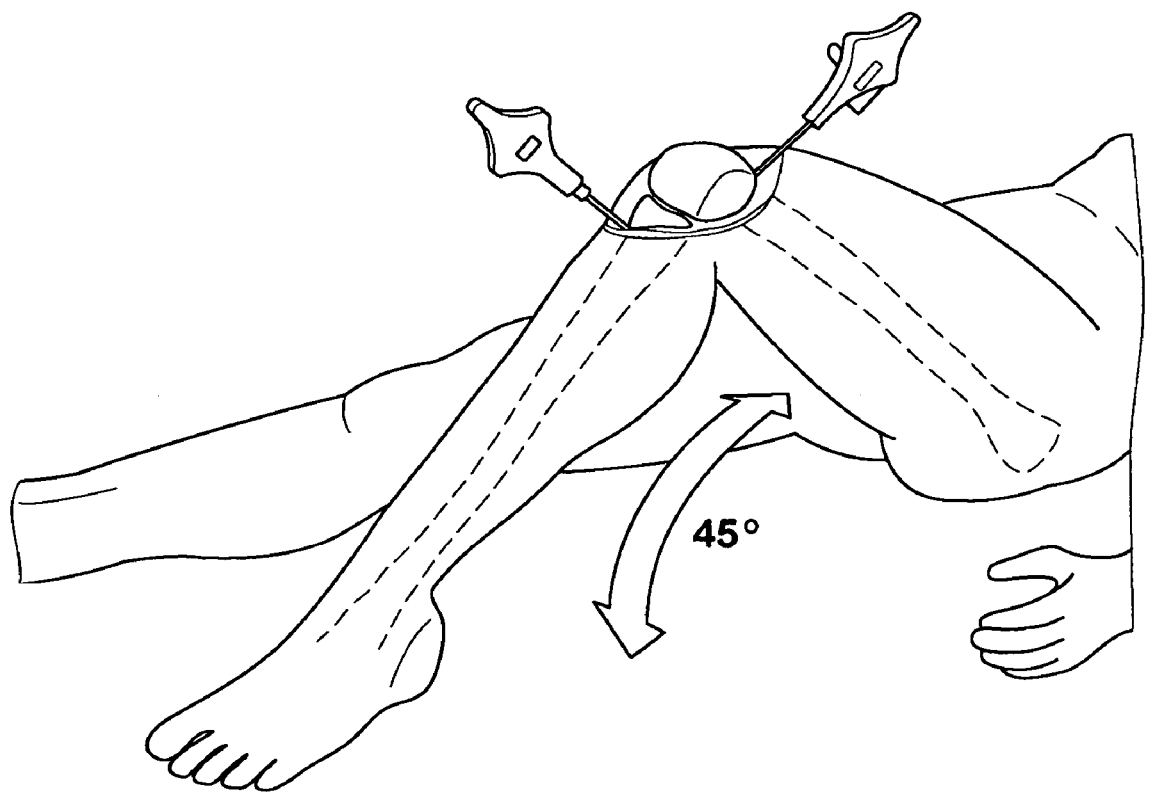
FIG. 8 is a view of a knee opened for surgery being manipulated to perform a kinematic analysis.

The kinematic assessment of the block 404 can be performed in a variety of ways. As an example, the kinematic assessment can display the translation and rotation values between the femoral and the tibial coordinate systems for a knee joint. The kinematic assessment also can include a graphical or tabular display of the various landmarks and axes of the joint in question. As shown in FIG. 8, the joint, in this case, the surgeon manipulates the knee joint and the various values are captured by the surgical navigation system 100. This include the range of motion including the flexion and extension values, the stability of the joint based on the medial/lateral displacement and the relative tibial-femoral varus/valgus angles and the distractibility based on the compression/distraction values. It is also possible that the surgical navigation system 100 can graphically display the distance between various points and axes as the joint is manipulated. This data can create a curve showing the relative stability and value of a gap in the joint across a range of motion or other manipulation of the joint, i.e. compression, rotation, etc. In addition it is possible for the surgical navigation system 100 to assist in the analysis of the kinematic data by displaying a graphical view of the joint along with a view of the selected curve from curves that have been recorded by the surgical navigation system 100. The process next proceeds to a block 406 that registers the image data to the mechanical axis. The block 406 performs this function in a similar manner to the block 204 described above. After the image has been registered, the control then passes to a block 408 that assists the surgeon to navigate the guide into position. The block 408 operates in a manner similar to the block 206 described above. After the resection procedure has been completed and either a trial implant or a final implant is been positioned in the joint and an outcome assessment of a block 410 is performed.

As noted previously, the system and method of the present invention can be used for aq wide variety of surgical procedures where it may be desirable to have an image enhancement to digital data displayed on a display screen. This includes surgery on the hip, shoulder, ankle, elbow, and similar joints.

INDUSTRIAL APPLICABILITY

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications, which come within the scope of the appended claims, are reserved.

I claim:

1. A system for registering two dimensional image data to intxa-operatively digitized landmarks obtained during a joint arthroplasty procedure on a patient having a joint in need of such a procedure comprising:
   a surgical navigation system capable of determining a position and an orientation of an object within a working volume, including a central processing unit, a display, a memory unit and a storage unit;
   means for importing the two dimensional image data for the joint into die memory unit;
   means for performing an intra-operative anatomical survey of the joint and an associated limb to digitize selected landmarks and determining a mechanical axis for the limb;
   means for registering the two dimensional image data to the mechanical axis and displaying a registered image of the mechanical axis and the two dimensional image data on the display; and
   means for assisting in guiding a cutting jig into position within the joint based on the landmarks while showing the registered two dimensional image data in relation to the landmarks, wherein the position and the orientation of the cutting jig can be tracked by the surgical navigation system.

2. The system of claim 1 wherein the assisting means displays the position of the cutting jig on the display relative to the registered two dimensional image data.

3. The system of claim 1 wherein the assisting means also displays a modified image based on the registered two dimensional image data showing a resection plane of a bone within the joint.

4. The system of claim 1 wherein the two dimensional image data is obtained pre-operatively.

5. The system of claim 1 wherein the two dimensional image data is obtained intra-operatively.

6. The system of claim 1 wherein the system includes means for performing an initial kinematics assessment of the joint.

7. The system of claim 6 wherein the registering means also registers the image data to the digitized landmarks, and to the kinematics assessment.

8. The system of claim 1 wherein the assisting means also displays digitized landmarks along with the registered two dimensional image data.

9. The system of claim 1 wherein the assisting means also displays a proposed resection plane on the registered two dimensional image data.

10. The system of claim 1 wherein the assisting means also displays the varus/valgus data and the extension/flexion data.

11. A method for registering two dimensional image data to intra-operatively digitized landmarks obtained during a joint arthroplasty procedure on a patient having a joint in need of such a procedure, the method comprising the steps of:

importing the two dimensional image data for the joint into memory of a surgical navigation system capable of determining the position and orientation of an object within a working volume wherein the surgical navigation system includes a display, a central processing unit and storage;

performing an anatomical survey of the joint and an associated limb;

digitizing selected landmarks based on the anatomical survey;

determining a mechanical axis for the limb based on the digitized landmarks;

registering the two dimensional image data to the mechanical axis and displaying the registered image data and mechanical axis on the display; and guiding a cutting jig into position within the joint using the surgical navigation system based on the landmarks.

12. The method of claim 11 including the additional step of displaying the position of the cutting jig on the display relative to the registered two dimensional image data.

13. The method of claim 11 including the additional step of displaying a modified image based on the two dimensional image data showing a resection of a bone within the joint.

14. The method of claim 11 wherein the two dimensional image data is obtained pre-operatively.

15. The method of claim 11 wherein the two dimensional image data is obtained intra-operatively.

16. The method of claim 11 including the additional step of performing an initial kinematics assessment of the joint.

17. The method of claim 16 wherein the two dimensional image data is also registered to the digitized landmarks, and to the kinematics assessment.

18. The method of claim 11 wherein the digitized landmarks are displayed along with the registered two dimensional image data.

* * * * *